United States Patent

Alden

[11] Patent Number: 5,863,294
[45] Date of Patent: Jan. 26, 1999

[54] FOLDED-END SURGICAL TUBULAR CUTTER AND METHOD FOR FABRICATION

[75] Inventor: Donald L. Alden, Sunnyvale, Calif.

[73] Assignee: FemRx, Inc., Sunnyvale, Calif.

[21] Appl. No.: 592,124

[22] Filed: Jan. 26, 1996

[51] Int. Cl.⁶ .................................................. A61B 17/32
[52] U.S. Cl. ........................................ 606/167; 606/170
[58] Field of Search .................... 606/170, 171, 606/167, 173, 172, 180, 159

[56] References Cited

U.S. PATENT DOCUMENTS

| | | | |
|---|---|---|---|
| 4,819,634 | 4/1989 | Shiber | 128/305 |
| 4,819,635 | 4/1989 | Shapiro | 128/305 |
| 4,850,354 | 7/1989 | McGurk-Burleson et al. | 128/305 |
| 5,007,917 | 4/1991 | Evans | 606/170 |
| 5,112,299 | 5/1992 | Pascaloff | 604/22 |
| 5,133,360 | 7/1992 | Spears | 128/754 |
| 5,269,798 | 12/1993 | Winkler | 606/170 |
| 5,330,480 | 7/1994 | Meloul et al. | 606/170 |

FOREIGN PATENT DOCUMENTS

| | | |
|---|---|---|
| 650479 | 6/1994 | Australia . |
| 0 499 465 A1 | 8/1992 | European Pat. Off. . |
| 28 48 314 | 5/1979 | Germany . |
| 2 205 045 | 11/1988 | United Kingdom . |

*Primary Examiner*—Michael Buiz
*Assistant Examiner*—Kevin Troung
*Attorney, Agent, or Firm*—Townsend and Townsend and Crew LLP

[57] ABSTRACT

The present invention provides a tubular surgical cutter fabrication method comprising forming one or more tabs which extend beyond an end of a tube. Each of the tabs is then folded across at least a portion of the end of the tube, and affixed in the folded position to form an end structure extending across the end of the tube. A cutting edge is imposed on the tube adjacent to the end structure, thereby providing a tubular surgical cutter having the structural reinforcement of a closed end without resorting to welding or otherwise attaching a closed end structure about the perimeter of the tube.

14 Claims, 2 Drawing Sheets

FOLDED-END SURGICAL TUBULAR CUTTER AND METHOD FOR FABRICATION

BACKGROUND OF THE INVENTION

1. Field of the Invention

This invention relates generally to surgical cutting devices, and in particular, provides a method for forming a tubular surgical cutter for use in endoscopy, arthroscopy, internal tissue resection, and other minimally-invasive surgical procedures, the method including forming the end of the cutter by folding tabs of tubal wall material.

Arthroscopic surgery techniques often involve manipulating a cutting probe through a small incision. For example, arthroscopic knee surgery often involves manually positioning the distal end of the probe against a tissue to be cut, typically against a meniscus in the knee joint. The piece of meniscus that is to be trimmed protrudes into an aperture formed in an outer tubular structure of the probe. An inner tubular structure rotates within this outer tubular structure, the inner tube including a chopping edge which sweeps by the aperture. Hence, the meniscus (or any other hard or soft tissues which protrude into the aperture) is sheared between the chopping edge of the inner tube and the edge of the aperture on the outer tubular structure.

U.S. patent application Ser. No. 08/136,426, and co-pending U.S. patent application Ser. Nos. 08/322,680, and 08/542,289 (Attorney Docket No. 16944-000130), the full disclosures of which are incorporated herein by reference, describe exemplary tissue resection devices having chopping mechanisms formed from cooperating tubular cutters. These exemplary tissue resectors include strip-cutting members which remove axial strips of tissue from an internal body cavity, the axial strips being chopped into tissue fragments by the chopping mechanism to facilitate evacuation of the tissue through the inner tube. These patent applications further describe a preferred method of use of the exemplary resection device for trans-cervical fibroid removal from the uterus and the like.

Known tubular cutters have typically been fabricated by drawing a cup of suitable material into the shape of a closed tube. This closed tube is then welded to the end of standard tubing of the appropriate size. The drawn cups are manufactured to sizes that allow the inner tubular structure to rotate smoothly inside the outer cup of the outer tubular structure, and generally provide small clearances for a good shearing action. After welding, the tube-cup assemblies are ground to create the desired opening, and also to impose the cutting edges in the tubal wall.

Although the above welded cup fabrication method has proven effective at producing tubular surgical cutters, the process does have certain drawbacks. The process requires a number of steps which must be very accurately performed to ensure cooperation between the inner and outer tubular structures. The cups must be drawn to sizes of very tight tolerance, and each must be precisely and welded to allow rotation. Achieving the required straightness in the welded structure typically requires fixturing, greatly increasing tooling costs. Furthermore, the fabrication process requires drawability, which limits the number of suitable materials and may also increase material costs.

For the above reasons, it is desirable to provide improved tubular surgical cutters and methods for their production. It would be particularly desirable if such tubular cutter production methods did not require welding of a separate cup onto the cutter tube. It would be especially beneficial if such cutter fabrication methods could be used for both the inner and outer cutter tubes, and if such fabrication methods relied on economical tube-forming procedures to provide a disposable tubular cutter assembly for use in a wide variety of minimally-invasive surgical procedures.

2. Description of the Background Art

U.S. Pat. No. 5,112,299 describes an arthroscopic surgical apparatus and method in which an elongate outer sheath member and an inner cylindrical cutting blade member are each provided with longitudinally-extending diametrically-opposed tabs having cutting edges. The tabs extend distally so that tissue positioned between the tabs is severed as the cutting blade member passes the sheath member. There is no suggestion that these tabs be folded to structurally reinforce the open ends of the cutting tubes.

U.S. Pat. No. 4,850,354 describes a surgical cutting instrument having inner and outer tubes. An opening having a corner is cut into at least one of the inner and outer tube, while the tubes themselves preferably include hemispherical ends.

U.S. Pat. No. 5,269,798, and European Patent Application Publication No. 0 499 465 A1 describe a surgical cutting instrument formed from cooperating inner and outer elongate tubular members, the distal end of each tubular member again including a hemispherical surface.

U.S. Pat. No. 4,819,635 describes a tubular microsurgery cutting apparatus having a hemispherically-ended outer tubular member in which a tubular inner sleeve reciprocates axially.

Australian Patent No. AU-B-85855/91 and German Patent No. 2848314 each describe surgical cutting instruments having rotary cutting tubes. U.S. Pat. No. 5,133,360 is generally relevant.

SUMMARY OF THE INVENTION

In a first aspect, the present invention provides a tubular surgical cutter fabrication method comprising forming one or more tabs which extend beyond an end of a tube. Each of the tabs is then folded across at least a portion of the end of the tube, and affixed in the folded position to form an end structure extending across the end of the tube. A cutting edge is imposed on the tube adjacent to the end structure, thereby providing a tubular surgical cutter having the structural reinforcement of a closed end without resorting to welding or otherwise attaching a closed cup about the perimeter of the tube.

Typically, a portion of tube material adjacent to the end of the tube is removed to form an aperture, and the cutting edge will generally be imposed on at least a portion of an axially-oriented surface bordering this aperture. This cutting edge will often be imposed while forming the aperture itself, typically by grinding or the like. This fabrication method provides a structure having a radial cutting action which is particularly useful for removing tissues and structures aligned with the axis of the tubular surgical cutter. In some embodiments, a cutting edge is also imposed on the end structure, allowing the tubular surgical cutter of the present invention to cut tissues at the cutter's distal surface.

The tubular surgical cutter fabrication method of the present invention may be used to produce an inner tubular cutter member, an outer tubular cutter member, or ideally, both. As with known tubular surgical cutters, the inner tubular member generally rotates relative to the outer tubular member, so that tissues which protrude through the aligned apertures are sheared as the inner aperture rotates.

In a preferred aspect, the tubular surgical cutter fabrication method according to the present invention comprises forming two tabs which extend from a tubal wall beyond an end of a tube. The tabs are folded across the end of the tube and toward each other and are attached together to form an end structure which extends across the end of the tube. A portion of the tubal material adjacent to the end is removed to form an aperture, and a cutting edge is imposed on a surface of the tube bordering that aperture.

Preferably, the folding step comprises bringing the two tabs together end-to-end, while the attaching step ideally comprises welding the tabs to each other. A wide variety of alternative tab-attaching methods could be used, including soldering, braising, spot-welding, or fastening the tabs together. Some of these attachment methods benefit from overlapping the tab ends. The preferred end-to-end welded tab attachment is facilitated by providing a flat, straight weld joint, providing a particularly strong end structure for reinforcing a tube end which would otherwise be weakened by an adjacent aperture.

In yet another aspect, the present invention provides a tubular surgical cutter comprising a tube having a proximal end, a distal end, a lumen therebetween, and an aperture adjacent to the distal end of the tube. An end structure extends from a first radial portion of the distal end of the tube to a second radial portion of the distal end of the tube. On one side, the first and second portions are separated by the aperture, while on the other side, roughly opposite the aperture, a gap separates the first and second portions. A cutting edge is disposed on an axially-oriented portion of a surface bordering the aperture.

The end structure spanning the aperture on the distal end of the tube reinforces the tubular surgical cutter where such reinforcement is most critical. Furthermore, the gap opposite the aperture greatly facilitates fabrication of the tubular surgical cutter by eliminating the need to weld a curving joint about the perimeter of the tube, or to otherwise draw the tube into a complex, curving shape. Advantageously, the end structure may be formed as folded tabs of tubal wall material, ideally being welded together in a simple end-to-end joint.

Typically, a cylindrical structure will be disposed coaxially with and rotatably relative to the tube, the cylindrical structure having a chopping edge which cooperates with the cutting edge to shear tissues which enter the aperture.

DETAILED DESCRIPTION OF THE SPECIFIC EMBODIMENTS

Figure 1:
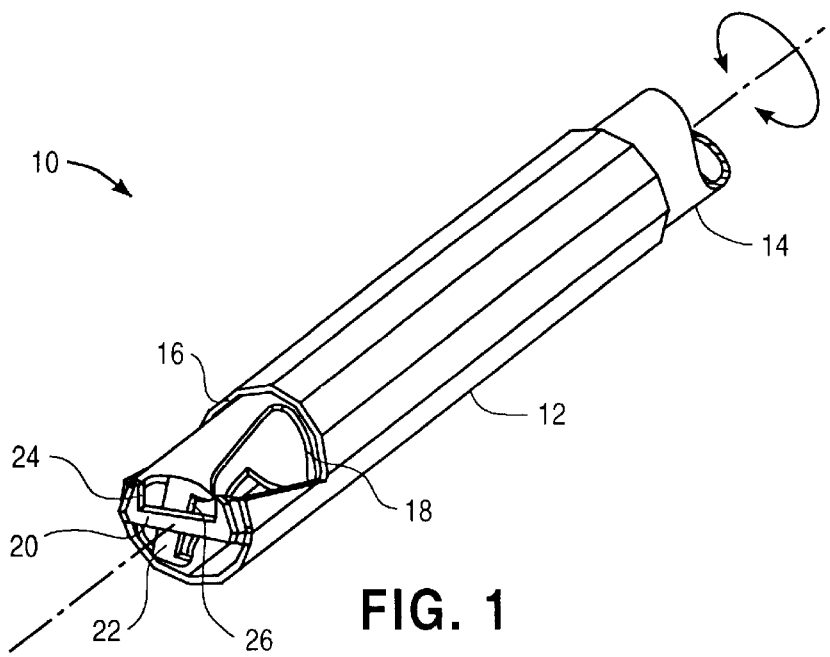
FIG. 1 is a prospective view of a tubular surgical cutter having inner and outer tubular structures which have been fabricated by the method of the present invention.

Referring now to FIG. 1, a tubular surgical cutter 10 includes an outer tubular member 12 in which an inner tubular member 14 is rotatably disposed. The outer and inner tubular members 12, 14 are very similar in shape and fabrication process, the outer tubular member 12 being, of course, larger in diameter so that the inner tubular member 14 is rotatably disposable therein.

The outer and inner tubular members 12, 14 each have an aperture 16, 18, the apertures intermittently aligned during the rotation of inner tubular member 14. However, as inner tubular member 14 rotates, the inner aperture 18 translates relative to the outer aperture 16 until the surfaces bordering the inner and outer apertures pass by each other, shearing off any tissues which protrude into the lumen of tubular surgical cutter 10. Typically, the sheared tissue is aspirated with irrigation fluid from the surgical site through this inner lumen to the proximal end of the surgical cutter (not shown).

Tubular members 12, 14 each have an end structure 20, 22 which reinforces the tubular structures across the open aperture. In the exemplary embodiment of FIG. 1, these end structures 20, 22 have end openings 24, 26. These end openings cooperate to shear tissues in a manner analogous to the inner and outer apertures described above. Specifically, tissues which protrude axially into the aligned end openings are sheared between outer end opening 24 and inner end opening 26 when inner tubular member 14 rotates. Preferably, the end openings and apertures are shaped so that the respective edges of the inner and outer tubular members slide past each other in a smooth, scissor-like shearing action, rather than passing by each other at a single discrete angular position.

It should be noted that the end structures 20, 22 each cover the rotational axis of tubular surgical cutter 10. Where the end structures are used to shear distal tissues, it is preferable that at least one, and ideally both of the end structures cover this axis to ensure that the tissue is fully severed, and that no strands remain which have not been subjected to the shearing action of the inner and outer tubular structures.

Figure 2:
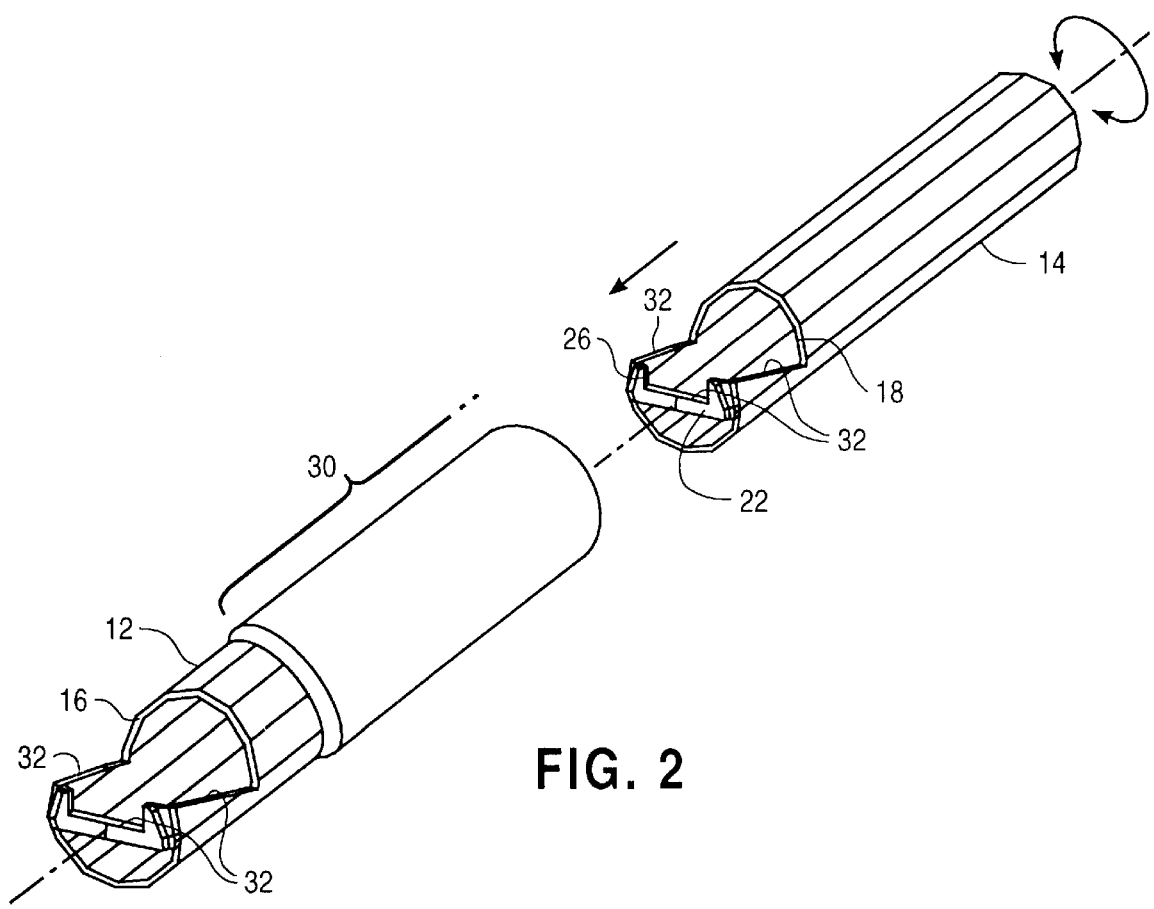
FIG. 2 is an exploded perspective view of the surgical cutter of FIG. 1, wherein the distal end of the outer tubular member has been drawn down to a smaller diameter to provide a tight tolerance only adjacent to the cutting edges, and to minimize friction along the length inner and outer tubular members.

Referring now to FIG. 2, the similar shapes of the inner and outer tubular members 12, 14 are clearly seen. To facilitate rotation between the inner and outer tubes, and to relax the straightness tolerances, the outer tube diameter increases along its proximal length 30. This increases the clearance between the inner and outer tubular members, and to improve the ability of the cutter to tolerate cutting debris which might otherwise become trapped between the two tubes. Tight tolerances are concentrated only at the distal ends, where required for optimal shearing performance. The axial change in cross-section is most easily provided by decreasing the distal diameter of a constant diameter tube. Cutting or chopping edges 32 may be imposed on the tubes after the apertures have been cut, or preferably, during the aperture-forming process by grinding away tube material until the desired aperture shape has been achieved.

Figure 3A:
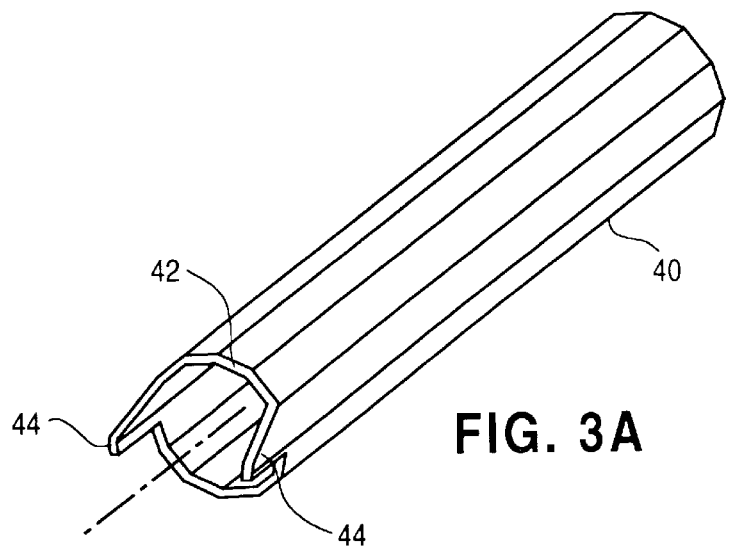
FIG. 3A–C illustrate a method for fabricating the inner and outer tubular members of the tubular surgical cutter of FIG. 1, according to the principles of the present invention.
Figure 3B:
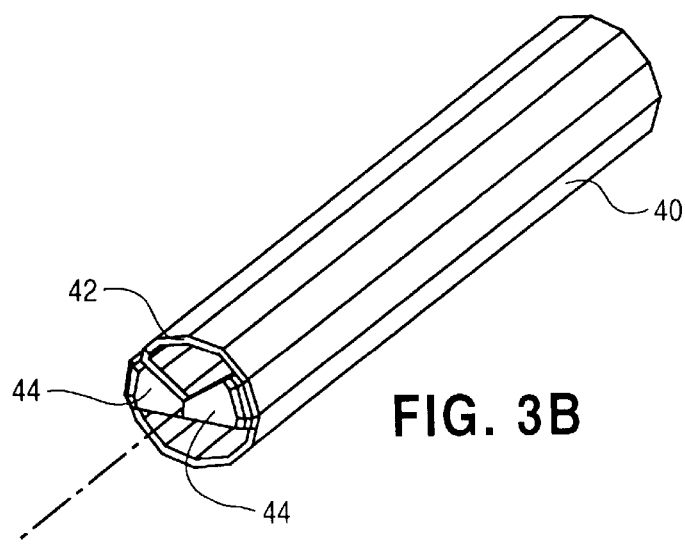
Figure 3C:
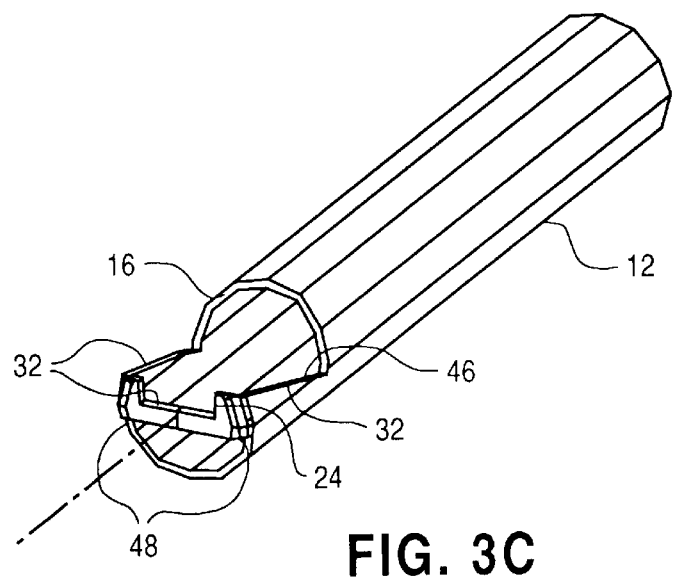

Referring now to FIGS. 3A–C, a cylindrical tube 40, typically comprising a high-strength conductive metal such as various alloys of stainless steel, steel, or the like, has material removed to leave a substantially flat end 42 and two protruding tabs 44. Tubing 40 will generally have an outer diameter in the range between 0.04" and 0.75", and a wall thickness in the range between 0.005" and 0.030". The removal of tube material may be performed by grinding, electro discharge machining (EDM), abrasion-cutting, shearing, or the like.

The use of two generally opposed tabs is preferable, although not required. Two tabs may be easily joined end-to-end with a simple, straight weld, and facilitates the use of a single large aperture to maximize the protruding tissue size which may be accommodated and sheared, which is particularly advantages for tissues having large dimensions. Alternatively, a single tab of sufficient length may be folded entirely across the end of tube 40 might be used. In still further alternatives, three or more tabs might be brought together to provide additional support to other radial areas of the tube, or to accommodate multiple smaller apertures radially disposed about the tube end.

The tabs 44 are folded across the end 42 and brought together end-to-end. As used herein, "folded across the end" means that the tab is folded in the direction of an alternate portion of end 42. This alternate portion need not be directly opposite the tab, and clearly, each tab need not extend all the way across the end of the tube by itself. It will be recognized that the folding process is simplified where each tab 44 defines a relatively small arc on the end of tube 42, as this minimizes the distortion of the circular cross-section of the tube when the tabs are folded.

Tabs 44 are preferably welded in their end-to-end folded configuration. Careful selection of the location and shape of tabs 44 provides a straight, planar weld joint. A wide variety of metal jointing techniques may alternatively be used, including soldering, braising, or where the tabs are allowed to overlap, spot-welding, rivets or other fasteners. The tabs may also be interlinked in a dovetail fashion where the two opposing ends mesh during the folding process.

Aperture 16 is most easily formed by grinding or abrasion-cutting material from tube 40 after the tabs have been welded together. This allows formation of the aperture and imposition of the cutting edge 32 simultaneously. The aperture is preferably cut so that axially-disposed aperture border surfaces 46 are angled relative to the axis as shown. This provides a smooth scissor-like shearing action when the inner tubular member is rotated. As used herein, "axially-disposed" means that the surfaces stretch from one axial position to another, but does not require that they be parallel to the tubular axis. Removal of the open portion 24 of the end structure is done in a manner similar to that used in forming aperture 16.

As seen in FIG. 3C, the completed end structure closes only the center portion of the tube to reinforce the cutting tube where it would otherwise be weakened by aperture 16. The fabrication process of the present invention thus satisfies tubular surgical cutter strength and fit requirements with simple, inexpensive welding, tooling, and tube forming techniques, without resorting to expensive fixturing (as is required to weld a sufficiently straight closed end cup to a tube). Additionally, by reinforcing only across the center of the tube, the method of the present invention utilizes simple trimming and bending methods which displace very little material, minimizing wasted resources.

Although the specific embodiment has been described in some detail, by way of illustration and for clarity of understanding, a variety of modifications, adaptations and alternatives will be obvious to those of skill in the art. For example, the folded tube end need not have a square profile, as a modified hemispherical shape (or other desired shape) may be produced from the folded tabs of the present invention. Therefore, the scope of the present invention is limited solely by the following claims.

What is claimed is:

1. A tubular surgical cutter fabrication method comprising:

forming at least one tab extending beyond an end of a tube;

folding each tab across at least a portion of the end of the tube;

affixing each folded tab in place to form an end structure which extends across the end of the tube; and imposing a cutting edge on the tube adjacent to the end structure.

2. A method as claimed in claim 1, wherein the tab forming step comprises cutting away tube material to form a plurality of tabs.

3. A method as claimed in claim 2, wherein the folding step comprises bringing the tabs together.

4. A method as claimed in claim 3, wherein the folding step further comprises bringing two tabs together end-to-end, and wherein the affixing step comprises welding the tabs to each other.

5. A method as claimed in claim 1, further comprising removing a portion of the tube material adjacent to the end of the tube to form an aperture.

6. A method as claimed in claim 5, wherein the cutting edge imposing step comprises forming an edge on an axially oriented surface bordering the aperture.

7. A method as claimed in claim 6, wherein the cutting edge imposing step further comprises forming an edge on the end structure.

8. A method as claimed in claim 6, further comprising inserting the tube within an outer tubular structure having a chopping edge so that the cutting edge and the chopping edge shear tissues which enter the aperture when the tube is rotated relative to the outer tubular structure.

9. A method as claimed in claim 6, further comprising inserting an inner tubular structure within the tube, the inner tubular structure having a chopping edge so that the cutting edge and the chopping edge shear tissues which enter the aperture when the inner tubular structure is rotated relative to the tube.

10. A tubular surgical cutter formed according to the method claimed in claim 1.

11. A tubular surgical cutter as claimed in claim 10, further comprising an inner tubular cutter formed according to the method of claim 1, the inner tubular cutter rotatably disposed within the tubular cutter.

12. A tubular surgical cutter fabrication method comprising:

forming two tabs which extend from a tubal wall beyond an end of a tube;

folding the tabs across the end of the tube toward each other;

attaching the tabs together to form an end structure extending across the end of the tube;

removing a portion of the tube material adjacent to the end to form an aperture; and imposing a cutting edge on a surface of the tube which borders the aperture.

13. A tubular surgical cutter fabrication method as claimed in claim 12, further comprising removing a portion of the end structure and imposing a cutting edge on the end structure bordering the removed portion.

14. A tubular surgical cutter fabrication method as claimed in claim 13, wherein the end structure covers a centerline of the tube after the portion is removed.

* * * * *